United States Patent [19]
Capuano et al.

[11] Patent Number: 5,734,097
[45] Date of Patent: *Mar. 31, 1998

[54] ANALYZER AND METHOD FOR MEASURING WATER IN LIQUIDS

[75] Inventors: Italo A. Capuano, Orange; Kenneth E. Creasy, Wallingford, both of Conn.

[73] Assignee: Olin Corporation, Cheshire, Conn.

[*] Notice: The term of this patent shall not extend beyond the expiration date of Pat. No. 5,693,538.

[21] Appl. No.: 598,865

[22] Filed: Feb. 9, 1996

Related U.S. Application Data

[63] Continuation-in-part of Ser. No. 521,782, Aug. 31, 1995.
[51] Int. Cl.[6] .................................................. G01N 1/22
[52] U.S. Cl. .......................... 73/61.43; 73/61.59; 436/39
[58] Field of Search ..................... 73/19.1, 19.12, 73/31.07, 61.43, 64.56, 61.59; 436/39, 177, 181; 203/3, 12, 14; 210/181, 188, 180, 767, 774

[56] References Cited

U.S. PATENT DOCUMENTS

| | | | |
|---|---|---|---|
| 2,715,833 | 8/1955 | Fulton et al. | 73/61.43 |
| 2,934,693 | 4/1960 | Reinecke et al. | 73/61.43 X |
| 3,037,374 | 6/1962 | Messinger | 73/61.43 |
| 3,799,846 | 3/1974 | Capuano | 204/1 T |
| 5,174,149 | 12/1992 | Grob et al. | 73/23.41 |
| 5,222,032 | 6/1993 | Fleming | 73/19.1 |
| 5,258,057 | 11/1993 | Baykut | 96/105 X |
| 5,266,496 | 11/1993 | Dacruz | 73/23.41 X |
| 5,454,258 | 10/1995 | Capuano | 73/61.43 |

*Primary Examiner*—Michael Brock
*Attorney, Agent, or Firm*—Dale Lynn Carlson Wiggin & Dana

[57] ABSTRACT

An analyzer and method for detecting and measuring the water content in a liquid sample in which the liquid sample is fed from its source to a head space chamber. The flow of liquid to the chamber is then halted, the water molecules in the liquid sample allowed to pass into the gaseous phase and escape from the liquid sample. A water-free carrier gas is caused to flow to the chamber and over the liquid to carry the gaseous water molecules to a moisture detector while the flow of the liquid sample to the head space chamber is halted.

20 Claims, 2 Drawing Sheets

5,734,097

ANALYZER AND METHOD FOR MEASURING WATER IN LIQUIDS

CROSS-REFERENCE TO RELATED APPLICATION

This application is a continuation-in-part of copending application Ser. No. 08/521,782 filed Aug. 31, 1995 and entitled "System and Method for Monitoring Volatile Species in Liquids".

BACKGROUND OF THE INVENTION

1. Field of the Invention

This invention relates generally to a method and analyzer for detecting and measuring the amount of water (moisture) in liquids. More particularly, this invention relates to a method and analyzer for detecting and measuring water in organic liquids of chemical process fluid streams.

2. Background

Many chemical reactions leading to the production of organic products such as isocyanates, polyethers, and others, should be conducted in the absence of water to prevent loss of yields, products contamination, and the possible damage to equipment due to the formation of solids. Additionally, in many cases where acidic materials such as hydrogen chloride, phosgene and chlorine are used or formed in a chemical process, introduction of water from external sources such as a heat exchanger or humid air must be excluded as water could react or ionize such species to form extremely corrosive conditions which could be detrimental to plant equipment and operation.

In order to assess if the presence of water in a process stream has reached a serious proportion and corrective action should be taken, it is desirable that a suitable analyzer be available for detecting the presence of water and providing a indication of the concentration thereof. However, to be effective with various chemical processes, the analyzer must be capable of measuring a wide range of concentrations, from a few parts-per-million (ppm) to percentage levels.

Conventional spectroscopic analyzers, such as near-infrared detectors, are neither suitable for the measurement of very low moisture concentrations (0–50 ppm), nor for concentrations higher than 1000 ppm of water. Such analyzers are not capable of detecting the low concentrations of water, and at the higher concentrations, the water tends to produce emulsions with organic systems such as benzene, chlorobenzene, toluene and the like, which are opaque to light, and render it impossible to make measurements. Electrochemical water analyzers, such as coulometric and amperometric, are suitable for low water concentration measurements (0–1000 ppm), but are not suitable for analysis when the concentration is above 1000 ppm due to lack of measurement linearity.

One solution to the problems set forth above is shown in U.S. Pat. No. 5,454,258, issued Oct. 3, 1995 to I. A. Capuano. As disclosed in that patent, an analyzer and method for detecting and measuring the presence of water in a liquid include passing a stream of the liquid to be monitored through a head space vessel. A dry gas is introduced into the head spaced vessel above the level of the liquid sample and picks up the water molecules in the space above the liquid sample and carries the water molecules to a mixing chamber. Dry gas is fed to the mixing chamber from a flow rate varying network that provides the proper flow rate of the dry gas to the mixing chamber to provide for a desired dilution of the sample in the mixing chamber. The resulting diluted sample stream leaves the mixing chamber and passes through a moisture detecting cell.

Although the apparatus and method disclosed in this U.S. Pat. No. 5,454,258 is satisfactory in many cases, if it is used in cases where the sample is taken from a system under pressure, the liquid sample from which the water vapor is extracted can not be directly returned to the pressurized system since the liquid sample is at atmospheric pressure.

SUMMARY OF THE INVENTION

In view of the above, it is an object of the present invention to provide an improved method and analyzer for detecting and measuring the concentration of water in a liquid.

A more specific object of the present invention is to provide an improved method and analyzer for detecting and measuring the concentration of water in an organic liquid that is capable of operating over a wide range of water concentrations.

Yet another object of the present invention is to provide an improved method and analyzer detector that is capable of detecting and measuring the concentration of water in an organic liquid chemical process stream.

Still another object of the present invention is to provide of a method and analyzer which is capable of detecting and measuring the concentration of water in an organic liquid chemical process stream wherein the sample of the liquid containing the water may be taken from and returned to a chemical process stream at points at which the process is under pressure.

A still further object of the present invention is the provision of an analyzer and method for detecting and measuring the water content of an organic liquid sample that is relatively simple and inexpensive in construction and operation.

These and other objects and advantages of the present invention may be achieved through the provision of a method for detecting and measuring the water content in a liquid sample which includes providing a flow of the liquid sample from its source to a head space chamber, interrupting said flow of said liquid sample to said chamber to provide a volume of liquid in said chamber, permitting the water molecules in said liquid sample to pass into the gaseous phase and escape from said liquid sample while in said chamber and the flow of liquid sample to said chamber is interrupted, subsequently sweeping a dry carrier gas over the surface of said liquid volume while said liquid flow is interrupted to carry the gaseous water molecules to a detector, and detecting the presence of water in the dry gas by means of a moisture detector and providing an electrical signal indicative of the amount of water in the liquid sample.

An analyzer for detecting and measuring the water content of a liquid sample according to the present invention may comprise a head space chamber in which the water molecules in the liquid sample pass into the gaseous phase and escape from the liquid, a first valve arrangement for controlling the flow of the liquid sample from its source to said head space chamber, a moisture detector for detecting the presence of water, a source of a water-free carrier gas, a second valve arrangement for controlling the flow of said carrier gas from its source to said head space chamber, and a controller for actuating the first valve arrangement to permit flow of said liquid from its source to said head space chamber and thereafter halting the flow thereto, and actuating the second valve arrangement after the halting of the flow of the liquid by said first valve arrangement to permit flow of said carrier gas to said head space chamber to carry the gaseous phase of the volatile species to said detector.

BRIEF DESCRIPTION OF THE DRAWINGS

The objects and advantages of the present invention will become more apparent by reference to the following detailed description and to the accompanying drawings in which.

DETAILED DESCRIPTION

Figure 1:
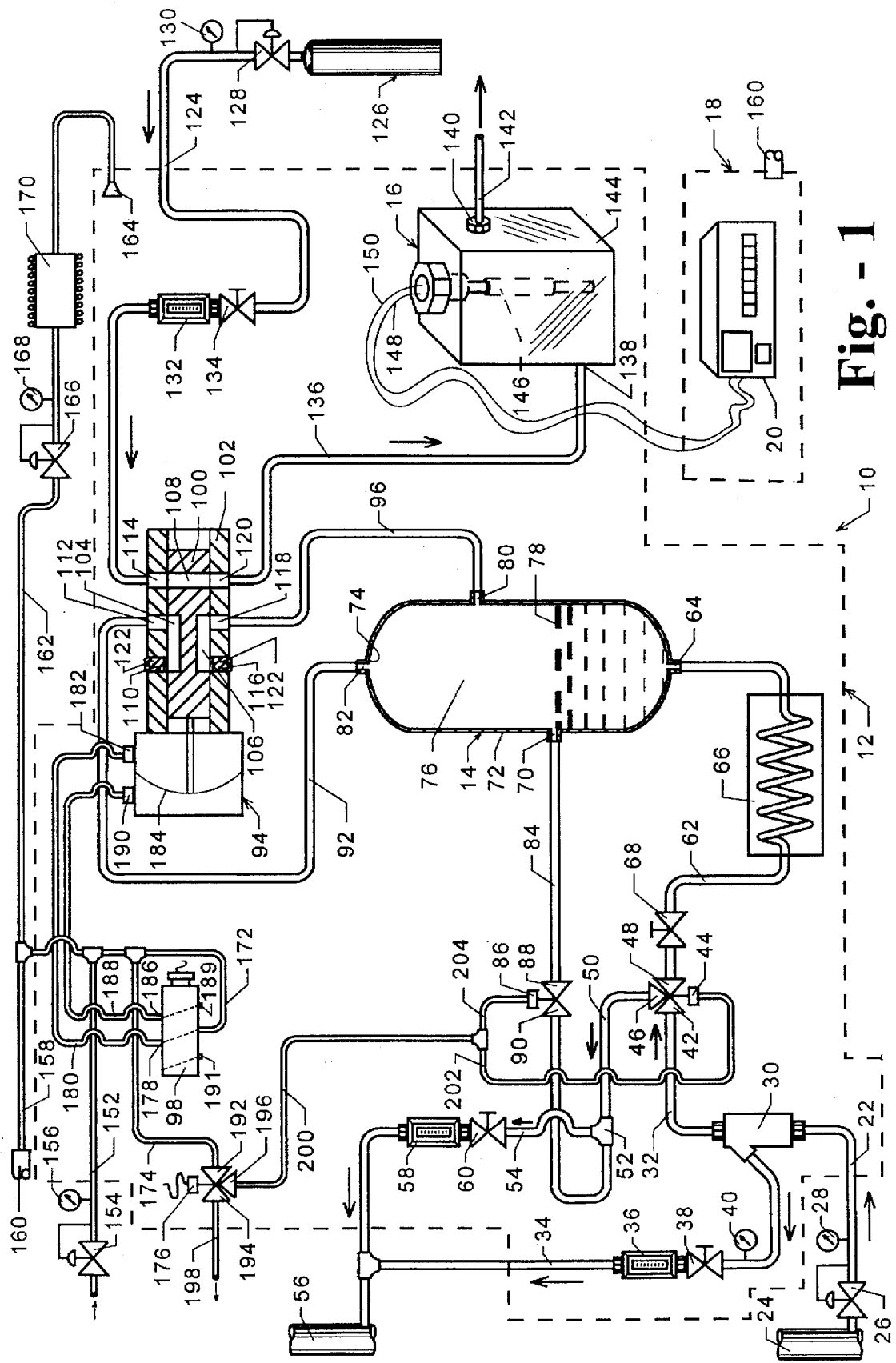
FIG. 1 is a schematic diagram of an analyzer embodying the principles of the present invention and showing the position of the valves at one stage of the operation of the analyzer.

Referring to the drawings and particularly to FIG. 1, there is shown an analyzer 10 that is capable of detecting moisture or water in a liquid, particularly an organic liquid. In general, the analyzer 10 of FIG. 1 comprises a sampling chamber 12 for providing a sample of the process liquid, including a head space vessel 14 for extracting water molecules from the liquid and a moisture detecting means 16 for detecting the moisture in the sample. The analyzer 10 also includes an electronic chamber 18 that may house suitable electronic components such as a controller or microprocessor 20 for controlling the operation of the analyzer and providing means for converting the signals from the detecting means 18 into output data.

More specifically, as shown in FIG. 1, the process liquid to be sampled enters the sampling section 12 of the analyzer 10 through an input line 22 that is attached to a source of the liquid stream to be sampled. The sample may be taken from any convenient location in the chemical process stream where the determination of the water content is of interest such as a line 24. The liquid sample may be taken at point in the process where the process liquid is under pressure, i.e., at a pressure greater than atmospheric. A pressure regulator 26 and pressure gauge 28 may be provided in the input line 22 to provide for a constant pressure of the incoming liquid.

The input line 22 may be connected to a filter 30 such as a Y-strainer that serves to remove any solid particles from the incoming liquid sample. The filter 30 may be of any appropriate type that is capable of preventing passage of solid particles into the filtered sample input line 32. A relatively large portion of the incoming liquid to the filter 30 is returned unfiltered back to a the chemical process stream through a first liquid return line 34.

A flow meter 36 with an adjustable flow restrictor 38 is provided in the liquid return line 34 with a pressure gauge 40 positioned in the line 34 downstream of the flow meter 36 and flow restrictor 38. The flow restrictor 38 may be of any suitable type capable of controlling the flow of the liquid therethrough and thus the pressure of the liquid upstream of the restrictor. A needle-type flow restricting valve is an example of a suitable type of restrictor 38. The pressure gauge 40, along with the flow meter 36 and the flow restrictor 38, provide a means to monitor and control the pressure of the sample passing through line 34 back into the process stream.

The filtered sample input line 32 is connected to an inlet port 42 of a sample inlet control valve 44. The sample inlet control valve 44 may be any type of three-way valve that can direct the flow of the incoming sample to one of two output ports. Preferably, the valve 44 is a three-way pneumatically operated, spring return, valve having three ports, an inlet port 42, a normally opened outlet port 46 and a normally closed outlet port 48. The valve 44 is actuated into its active or "on" position by pneumatic fluid such as operating air and returned to its closed or "off" position by a spring. In the closed position, the valve 44 provides communication between the inlet port 42 and the normally opened outlet port 46. Upon the application of pneumatic fluid to the valve, the valve is activated into its open position in which it provides communication between the inlet port 42 and the normally closed outlet port 48, while the outlet port 46 is closed. Upon removal of the flow of pneumatic fluid to the valve 44, the valve 44 returns to its closed position.

A filtered sample return line 50 is connected to the normally open port 46 of the sample inlet control valve 44 with its other end connected to a tee 52 to which is connected a filtered sample outfeed line 54 which leads back to the process stream and serves to return the liquid sample thereto. The filtered sample outfeed line 54 may be directly connected to an appropriate point in the process stream or may join with the first liquid return line 34. The pressure of the process liquid at the point the liquid sample is returned may be greater than atmospheric, but at a point at which the pressure is lower than the pressure of the process liquid at the point at which the liquid sample is withdrawn. The outfeed line 54 is connected to the process stream at a point such as line 56 of the process stream that is at a lower pressure than the incoming sample from the line 24 into the input line 22. The outfeed line 54 may include a flow meter 58 with a flow restrictor 60 to regulate the flow of the outgoing liquid.

A sample infeed line 62 is connected at one end to the normally closed port 48 of the sample inlet control valve 44 and at its other end to an inlet port 64 of the head space chamber 14. The sample infeed line 62 contains a heat exchanger 66 that serves to heat the incoming liquid sample as it passes to the head space chamber 14 from the sample inlet control valve 44.

The line 62 also contains a flow adjustment valve 68, positioned upstream of the heat exchanger 66, for adjusting the flow of the incoming liquid stream to the head space chamber 14. This valve 68 preferably is a micro-needle valve, although any suitable type of flow adjuster may be used.

The inlet port 64 of the head space chamber 14 is positioned in the bottom of the head space chamber 14 as shown. The head space chamber 14 includes a liquid outlet port 70 in its side wall 72 positioned in a horizontal plane intermediate the plane of the top and bottom of the chamber 14. The internal volume of the chamber 14 between the horizontal plane of the outlet port 70 and the inside surface 74 of the top portion of the chamber 14 provides a head space area 76 above the level 78 of the liquid sample in the chamber 14 for the water to pass into a gaseous phase above the liquid sample.

A gas outlet port 80 is positioned in the side wall 72 of the head space chamber 14 vertically above the horizontal plane of the axis of the liquid outlet port 70. A gas inlet port 82 is provided at the top of the of the chamber 14 as shown.

The head space chamber 14 may be formed from any suitable receptacle of a material capable of containing the particular liquid sample to be analyzed and which is non-corrosive with respect to the liquid being sampled. Preferably, the chamber is fabricated from stainless steel, or Hastalloy C or Monel if the liquid sample is corrosive.

One end of a liquid sample stream outlet line 84 is connected to the liquid outlet port 70 of the head space chamber 14. The other end of the outlet line 84 is connected to the tee 52 to which the liquid outfeed line 54 is connected so that liquid sample stream may flow through the line 84 and line 54 from the head space chamber 14 to the process stream at the point 56. A shut-off valve 86 is positioned in the liquid sample stream outlet line 84 at a point adjacent to the outlet port 70. The valve 86 may be may be any suitable type of shut off valve capable of ultimate control by the microprocessor 20. Preferably, the valve 86 is a two-way, pneumatically actuated, spring returned, valve having a normally closed inlet port 88 facing upstream in the line 84 and an outlet port 90 facing downstream in the line 84. Alternatively, other types of valves may be used such as a solenoid actuated on-off switching valve that is controlled by the microprocessor 20.

The gas inlet port 82 of the head space chamber 14 has one end of an incoming dry gas flow line 92 connected thereto with the other end of the line 92 connected to a fluid control valve 94. The gas sample outlet port 80 of the head space chamber 14 has one end of a gas sample flow line 96 connected thereto with the other end of the line 96 also connected to the fluid control valve 94.

The fluid control valve 94 is preferably a commercially available, six-port slider plate valve that is pneumatically actuated between a deactivated position and an activated position. A solenoid valve 98, controlled by the microprocessor 20, may control the supply of pneumatic fluid such as instrument air to the valve 94 to cause the movement of the valve 94 between its two positions.

The fluid control valve 94 may include a slider plate 100 movable in a body 102 between the deactivated and activated positions of the valve 94. The slider plate 100 may include a first groove or passage 104 in one surface of the slider plate 100. A second groove or passage 106 may extend axially in the opposite surface of the slider plate 100 as shown. A through-bore or passage 108 extends between the two surfaces of the slider plate 100. The body 102 of the fluid control valve 94 may include six ports 110, 112, 114, 116, 118 and 120. The ports 110, 112 and 114 are positioned in one side of the body 102 and the ports 116, 118 and 120 are positioned in the opposite side of the body 102 as shown. The fluid control valve 94 is modified by eliminating or blocking the ports 110 and 116 that are diametrically opposite to each other as shown. These ports 110 and 116 may be rendered inactive by inserting suitable plugs 122 therein.

In the deactivated or "off" position of the valve 94, shown in FIG. 1, the slider plate 100 is in its retracted position and the passage 104 connects the ports 110 and 112, and thus is inactive since port 110 is plugged. The passage 106 connects the ports 116 and 118, and is also inactive in the "off" position since port 116 is plugged. The through-bore or passage 108 in the slider plate 100 connects the ports 114 and 120.

Figure 2:
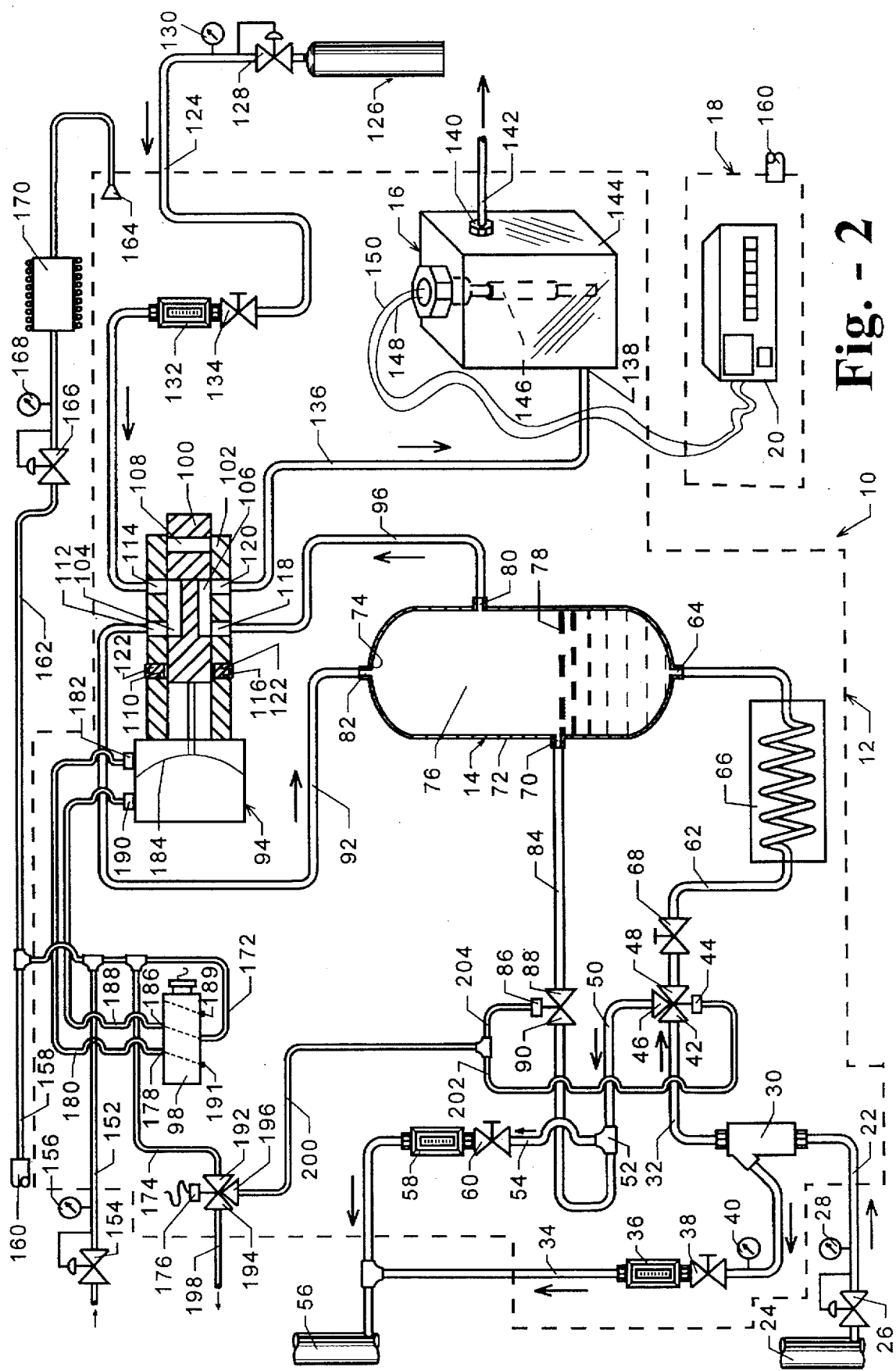
FIG. 2 is a schematic diagram of the analyzer of FIG. 1 showing the position of the valves during another stage of the operation of the analyzer.

When the valve 94 is actuated into its activated, or "on" position, the slider plate 100 is extended outwardly, to the right as viewed in FIG. 2, so that the passage 104 connects the ports 112 and 114 and passage 106 connects the ports 118 and 120. The ports 110 and 116 are blocked and the through-bore or passage 108 is not in communication with any of the ports.

The gas flow line 92, having one end connected to the gas inlet port of the head space chamber 14, has its other end connected to the port 112 of the fluid control valve 94. The carrier gas line 96, having one end attached to the gas outlet port 80 of the head space chamber 14, has its other end connected to the port 118 of the fluid control valve 94.

A water-free carrier fluid, preferably a dry gas such as dry nitrogen or dry air, is introduced into the system by means of an incoming dry gas line 124. The dry gas line 124 is connected at its incoming end to a suitable source of the dry gas such as a tank 126 or other source that may be readily available on site at the plant. The other end of the incoming dry gas line 124 is connected to the port 114 of the fluid control valve 94. The line 124 may includes a pressure regulator 128, and a pressure gauge 130 adjacent the source 126 of the dry gas. A flow meter 132 and associated flow restrictor such as a needle valve 134 are positioned in the incoming dry gas line 124 downstream of the pressure gauge 130. The pressure regulator 128 serves to control the pressure of the incoming dry gas while the flow meter 132 and associated flow restrictor 134 provide a means to monitor and control the flow the incoming dry gas.

A flow line 136 extends from the port 120 of the fluid control valve to the inlet 138 of the moisture detecting cell 16. An outlet 140 of the moisture detecting cell 16 has a vent line 142 connected thereto which is vented to the atmosphere or to a plant scrubber (not shown).

The moisture detecting cell 16 and its operation may be of the type described in U.S. Pat. No. 3,799,846, issued Mar. 26, 1974, to I. A. Capuano and entitled "Moisture Analysis Method," and U.S. Pat. No. 5,454,258, issued Oct. 3, 1995, to I. A. Capuano and entitled "Broad Range Moisture Analyzer and Method". The disclosures of both U.S. Pat. Nos. 3,799,846 and 5,454,258 are incorporated herein by reference in their entirety. While reference may be made to those patents for a detailed explanation of the construction and operation of a suitable moisture detecting cell, briefly, the cell 16 is an electrolytic cell and utilizes closely spaced electrodes coated with a film of a hygroscopic material which is substantially non-conductive electrically and non-reactive with the material being sampled, but reactive with water to form an electrically conductive substance. The electrically conductive substance, in turn, upon the application of a potential difference (voltage) across the electrodes, decomposes electrolytically into the elements of water with the regeneration of the hygroscopic material. The resulting electrolysis current is proportional to the water content in the sample being tested.

In general, the cell 16 includes a cell block 144 and a rod-like sensor 146 that extends into the cell block 144. The sensor 146, as well as the cell block 144, may be fabricated from a suitable dielectric material. The cell block 144 is preferably fabricated from clear polymethylmethacrylate that will permit the visual inspection of the electrodes. The sensor 146 is preferably fabricated from polyethylene that is an effective insulator and has good wettability and absorption characteristics for the hygroscopic material. Other plastics such as polyvinyl chloride, polymethylmethacrylates and polystyrene are also suitable.

Two spaced lead wires 148 and 150 extend down through bores (not shown for the sake of clarity) in the sensor 146 and are connected to two electrode wires (not shown) which are wound around the outside of the portion of the sensor which is positioned in the cell block 144 in threads (not shown). The lead wires 148 and 150 may be of any suitable electrically conductive material, although platinum is preferred because of possible corrosion. The electrode wires are preferably platinum, but any of the platinum group metals or their alloys may be used.

The length of the sensor having the exposed platinum electrode wires wound in the double threads forms an electrode area that is provided with a film of a hygroscopic material. The hygroscopic material is substantially non-conducting and non-reactive with the fluid being sampled, but reacts with water to form an electrically conducting substance. When an electrical voltage differential is applied across the electrodes, the electrically conducting substance decomposes into the elements of water with the regeneration of the hygroscopic material.

Hygroscopic materials suitable for use as the film on the sensor include phosphorus pentoxide, sodium hydroxide, potassium carbonate, potassium hydroxide, potassium metaphosphate and silicic acid, it being understood that the material selected should be one that is non-reactive with the components of the fluid being sampled except for water. Phosphorous pentoxide is eminently suited for most sample materials and is preferred.

By way of example, when using a phosphorous pentoxide film on the two electrodes, the application of a potential difference across the electrodes causes the cell to operate on the following electrochemical principle:

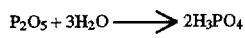

and

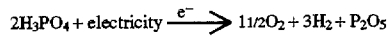

with the electrolytic current produced in the measurement being proportional to the water or moisture concentration in the sample.

The current produced by the electrolysis in the moisture detecting cell 16 is carried by the pair of lead wires 148 and 150 to the microprocessor 20 in the electronic chamber 18. The microprocessor 20 may include an appropriate power source, preferably a 75 volt D.C. regulated power supply, as well as circuitry for converting the current signal for output to a recorder (not shown).

A suitable source (not shown) of a pneumatic operating fluid such as instrument air is introduced into the analyzer 10 by means of an incoming operating air flow line 152. A pressure regulator 154 and pressure gauge 156 is provided in the incoming operating air flow line 152 to regulate the pressure of the incoming operating air. The incoming operating air flow line 152 splits into a plurality of lines including a purge line 158 that has an outlet 160 positioned in the electronics chamber 18 to provide a purge of air to the chamber housing the microprocessor 20 and any other electronic components. The operating air flow line 152 also splits into a heating air line 162 that has an outlet 164 in the sampling chamber 12. A pressure regulator 166 and pressure gauge 168 are provided in the heating air line 162 to regulate and monitor the pressure of the heating air in the line 162. A heater 170 is also provided in the line 162 to heat the incoming air to the chamber 12 so that the temperature of the chamber 12 may be maintained at a constant level. The heater 170 may be any suitable type such as an electric heater having controls including a sensor located within the chamber 12 to control its operation and maintain the temperature within the chamber 12 at the desired constant level.

The incoming operating air flow line 152 also splits into a first operating air line 172 that is connected to the solenoid valve 98 and a second operating air line 174 that is connected to a solenoid valve 176. The solenoid valve 98 is preferably a conventional 4-way solenoid valve electrically connected to the microprocessor 20 for operation. The first outlet port 178 of the solenoid valve 98 is connected by a line 180 to the inlet opening 182 to the front of an operating diaphragm 184 in the fluid control valve 94. The second outlet port 186 of the solenoid valve 98 is connected by a line 188 to the inlet opening 190 to the rear of the diaphragm 184. In the de-energized, or "off", position of the solenoid valve 98, the operating air entering the valve 98 from the line 172 is caused to flow out of the valve 98 through the port 178 into line 180 to the forward side of the diaphragm of the valve 94. The port 186 to which the line 188 is connected, communicates with a vent port 189 in the valve 98. The port 189 is open to the atmosphere. Thus, in the de-energized position of the valve 98, operating air flows from line 172 through the solenoid valve 98 out through port 178 into line 180 into the inlet opening 182 into the area in front of the diaphragm 184. The air in front of the diaphragm 184 forces the diaphragm 184 into its rearward position shown in FIG. 1. The area behind the diaphragm 184 is vented to the atmosphere through line 188, through the valve 98, and out through the vent port 189. The diaphragm 184, as is well know in the art, is connected to the slider plate 100 of the valve 94, and when the diaphragm 184 is in its rearward position, the slider plate 100 is held in its retracted position as shown in FIG. 1.

In the energized or "on" position of the solenoid valve 98, operating air flows from line 172 through the solenoid valve 98 into line 188 and then to the rear of the diaphragm 184 in the fluid control valve 94. At the same time, the port 178, to which line 178 is connected, communicates with a vent port 191 in the valve 98. The port 191 is open to the atmosphere. Thus, when the solenoid valve is energized into its "on" position, operating air flows through line 188 to the rearward side of the diaphragm 184, causing the slider member 100 in the fluid control valve 94 to move to the right as view in the drawings into its extended position. The air in the forward side of the diaphragm 184 is vented to the atmosphere through line 180, valve 98, and the vent port 191.

The line 174, which is split off from the incoming operating air flow line 152, is connected to an inlet port 192 of the solenoid valve 176. The solenoid valve 176 may be a conventional three-way solenoid valve actuated by an electrical signal from the microprocessor 20 between an de-energized or "off" position and an energized or "on" position. The solenoid valve 176 includes three ports, a normally closed inlet port 192, a normally opened port 194 and a common port 196. In the de-energized or "off" position, the port 192 is normally closed while port 194 is normally open and in communication with the port 196. A vent line 198 is connected to the port 194. The third port 198 is the common port and has connected thereto an air line 200 which in turn is connected by branch lines 202 and 204 to the valves 44 and 86. When the solenoid valve 176 is energized, port 192 is connected with the common port 198 while port 192 is closed so that operating air flows from line 174, through the solenoid valve 176 and lines 200, 202 and 204 to the valves 44 and 88 to cause their actuation.

In operation, when the analyzer 10 is in the "inactive" position, between the analytical cycle and before the replenishment of the liquid sample in the head space chamber 14, the valves 44, 86 and 94, are in their "off" or deactivated position as shown in FIG. 1. With the valves so positioned, a liquid sample stream flows from the process line 24 through the line 22 to the filter 30. A portion of the liquid sample stream returns to the process line 56 through line 34 while another filtered portion passes from the filter 30 into the filtered liquid sample incoming flow line 32. As the valve 44 is in its inactive or "off" position, the fluid stream in line 32 passes into port 42 of the valve 44 and out of the valve 44 through port 46 into the line 50 and then into line 54 wherein that portion of the liquid sample stream flows back into the process line 56.

Also, in the "inactive" mode of the analyzer 10, the solenoid valve 98 is in its de-energized position wherein operating air flows from lines 152 and 172 through the valve 98 into line 180 to the forward side of the diaphragm of the fluid control valve 94, thereby maintaining the valve 94 in its deactivated position with the slider member 100 in the retracted position as shown in FIG. 1. With the fluid control valve 94 in such position, the dry gas from the source 126 flows through line 124 to the port 114 of the valve 94, through passage 108, and exits the valve 94 through port 120 into line 136. The dry gas flows from line 136 through the detector 16 and exits the detector 16 into the vent line 142.

The first step at the start of a sampling cycle is to replenish the liquid sample in the head space chamber 14. This is accomplished by energizing the solenoid valve 176 to permit operating air to flow to both valves 44 and 86 to actuate those valves into their "on" or active positions. By energizing the solenoid valve 176 into its "on" or active position, operating air flows from its source through lines 152 and 174 to the inlet 192 of the solenoid valve 176 and exits the valve 176 though port 196 into line 200. The operating air then flows from the line 200 through lines 202 and 204 to the valves 44 and 86 respectively to cause their simultaneous actuation into the "on" or active positions. During this phase of operation of the analyzer, the solenoid valve 98 remains de-energized thereby maintaining the fluid control valve 94 in its inactive position.

With the valves 44 and 86 actuated into their active positions, the liquid sample stream from the filter 30 can pass into line 32 to the inlet of the valve 44, exit the valve 44 through port 48 into line 62 wherein the liquid sample will flow through the heat exchanger 66 into the head space chamber 14 through the inlet 64. The heat exchanger 66 in the line 62 helps to raise the temperature of the incoming liquid sample to the point at which it can be maintained at the desired temperature by the thermostated chamber 12. The incoming liquid sample replaces the liquid previously in the head space chamber 14 and fills the chamber up to the level of the outlet port 70. Excess liquid sample passes out of the chamber 14 through the outlet port 70 into the line 84 where it flows to the valve 86. As the valve 86 is in its actuated or "on" position, the excess liquid sample can passes through the valve 86 and into line 54 and back to the line 56 of the process stream. With the fluid control valve 94 in its off position, liquid will not be able to flow in lines 92 and 96 since these lines are blocked by the valve 94.

The valves 44 and 86 are maintained in their "on" positions for a sufficient amount of time to ensure that the liquid sample in the head space chamber 14 is completely replenished. Generally, to ensure reliable analysis, the valves 44 and 86 may remain "on" until at least three volumes of new liquid sample have passed through the head space chamber 14, and preferably at least five volumes have passed through. The amount of time necessary to accomplish this may be determined by calculations using the known volume of the liquid portion of the head space chamber 14 and the flow rate of the incoming liquid sample.

After the liquid sample in the head space chamber 14 has been sufficiently replenished, the valves 44 and 86 are caused to be actuated back into their "off" position. This is accomplished by de-energizing the solenoid valve 176 so that it moves back into its inactive position that cuts off the flow of operating air to the valves 44 and 86, permitting the valves 44 and 86 to return to their inactive positions. This effectively closes the port 48 of the valve 44 and opens port 46 so that the flow of the incoming sample stream to the head space chamber 14 is halted. The incoming sample stream from line 32 flows out of the valve 44 through the port 46 into the return lines 50 and 54 and returns to the process stream. The valve 86 is closed so that there is no flow therethrough so that the fresh liquid sample in the chamber 14 can come to rest. The valves 44, 86 and 94 remain in their inactive positions, with the liquid sample in the head space chamber 14 remaining at rest, for a sufficient period of time to permit the water molecules in the liquid to pass into the gaseous phase and escape from the liquid into the area 76 above the liquid level 78 in the head space chamber 14 and come into partial or complete equilibrium. Complete equilibrium may not be required depending upon the concentration of the water in the liquid sample since repetitive results will be achieved due to the controlled conditions of the system.

The chamber 12, in which the head space chamber 14 is located, may be maintained at an elevated temperature to aid in forcing the gaseous water molecules out of the liquid sample in the head space chamber. The heat exchanger 66 in the incoming line 62 to the head space chamber helps to raise the temperature of the incoming liquid sample to the elevated temperature.

With the liquid sample in the head space chamber 14 at rest, and after the water molecules have passed into the gaseous phase and escaped from the liquid into the area 76 above the liquid level 78 and come into partial or complete equilibrium, the analytical portion of the monitoring cycle may be initiated. When it is desired to perform an analysis, the fluid control valve 94 is actuated into its "on" position. This is accomplished by energizing the solenoid valve 98 into its "on" position. In the energized or "on" position of the solenoid valve 98, operating air passes into the valve 98 from line 172 and exits through port 186 into line 188 through which it flows to the rearward side of the diaphragm 184 of the valve 94, forcing the diaphragm 184 into its forward position and the slider member 100 into its extended position as shown in FIG. 2.

With the fluid control valve 94 activated into its "on" position, the dry carrier gas will flow from its source 126 through line 124 into the valve 94 through port 114. The carrier gas will pass through passage 104 and exit the valve 94 through port 112 into the line 92. The dry gas flows in line 92 to the head space chamber 14 where it enters the chamber 14 through port 82. The dry gas sweeps over the surface of the liquid sample in the chamber 14 and carries the gaseous water molecules in the head space area 76 out of the head space chamber 14 through the gas outlet 80 into the line 96. The dry gas carries the gaseous water molecules from the head space area 76, along with any gaseous molecules present in the line 96, to the fluid control valve 94 where it enters the valve 94 through the port 118. The dry gas with the water molecules passes through passage 106 in the valve 94, and exits the valve 94 through the port 120 into the line 136 to the detector 16. The volume of the head space area 76 and the internal volume of the length of the line 96 provides a known fixed volume of gaseous water molecules which passes through the moisture detecting cell 16. The water molecules react with the film in the cell 16 producing a current proportional to the amount of water reacting with the film. The current signal is carried to the microprocessor by the lead wires 148 and 150 where the signal may be processed for a readout showing the actual concentration of water in the liquid sample.

After an appropriate period of time sufficiently long to ensure that the carrier gas has carried the water molecules from the head space chamber 14 to the moisture detecting cell 16, the fluid control valve 94 is returned to its "off" or deactivated position ready for the start of the next cycle. The valve 94 is actuated into its off position by de-energization of the solenoid valve 98 that permits the valve 98 to return to its de-energized or "off" position. In the "off" position of the solenoid valve 98, operating air is passed from lines 152 and 172 through the solenoid valve 98 and out of the port 178 into line 180. Line 180 directs the operating air to the front side of the diaphragm 184 of the fluid control valve 94 so that the diaphragm 184 is moved rearward (to the left as viewed in FIG. 2) thereby retracting the slider member 100 into the retracted position and cutting off flow of the dry gas to the head space chamber 14.

By way of example, when utilizing the above described analyzer for detecting and measuring water in toluene, the temperature of the toluene sample in the head space chamber 14 may be maintained constant at a temperature between about 50° to about 70° C. The toluene sample should remain at rest in the head space chamber for about 110 seconds. Dry air or nitrogen may be used as the carrier gas at a flow rate of 2 liters per minute. This will provide a flow rate of the gaseous sample containing the water molecules from the head space chamber 14 to the detector 16 of 200 ml/min.

While the invention has been described above with reference to a specific embodiment thereof, it is apparent that many changes, modifications and variations can be made without departing from the concepts disclosed herein. Accordingly, it is intended to embrace all such changes, modifications and variations that fall within the spirit and broad scope of the appended claims.

What is claimed is:

1. A method for detecting and measuring the water content in a liquid sample comprising the steps of:
    a. providing a flow of the liquid sample from its source to a head space chamber at a constant temperature,
    b. interrupting said flow of said liquid sample to said chamber to provide a volume of liquid in said chamber,
    c. permitting the water molecules in said liquid sample to pass into the gaseous phase and escape from said liquid volume while in said chamber and the flow of liquid sample to said chamber is interrupted,
    d. subsequently sweeping a dry carrier gas over the surface of said liquid volume prior to the water molecules in the liquid sample and the water molecules escaped from the liquid volume reaching equilibrium while said liquid flow is interrupted to carry the gaseous water molecules to a detector, and
    e. detecting the presence of water in the dry gas by means of a moisture detector an providing and electrical signal indicative of the amount of water in the liquid sample.

2. The method of claim 1 wherein the liquid sample is taken from a point in its source where said liquid sample is at a pressure greater than atmospheric.

3. The method of claim 2 further comprising returning the liquid sample in said head space chamber to its source at a point that has a pressure greater than atmospheric pressure after said detecting.

4. The method of claim 2 further comprising returning the liquid sample in said head space chamber to its source after said detecting, said liquid sample being returned at a point in its source that has a pressure greater than atmospheric pressure and less than the pressure at which the liquid taken.

5. The method of claim 1 further comprising discontinuing the flow of carrier gas over the liquid sample, and thereafter resuming the flow of the liquid sample to said head space chamber to replenish the liquid sample therein.

6. The method of claim 1 further comprising discontinuing the flow of carrier gas over the liquid, and thereafter repeating the steps of claim 1.

7. The method of claim 1 wherein said flow of said liquid sample is provided to said chamber by opening a valve in an inlet line connected to said chamber and opening a valve in an outlet line from said chamber, and said flow is interrupted by closing said valves in said inlet line and said outlet line.

8. The method of claim 1 wherein the detecting of the presence of water includes passing the dry gas carrying the water molecules through an electrolytic moisture detecting cell.

9. The method of claim 1 further including maintaining the liquid sample in said head space chamber at a constant elevated temperature.

10. An analyzer for detecting and measuring the water content of a liquid sample comprising:
    a. a head space chamber in which the water molecules in the liquid sample pass into the gaseous phase and escape from the liquid,
    b. a first valve arrangement for controlling the flow of the liquid sample from its source to said head space chamber at a constant temperature,
    c. a moisture detector for detecting the presence of water,
    d. a source of a water-free carrier gas,
    e. a second valve arrangement for controlling the flow of said carrier gas from its source to said head space chamber, and
    f. a controller for actuating the first valve arrangement to provide a fixed volume of said liquid from its source to said head space chamber and thereafter halting the flow thereto, and actuating the second valve arrangement after the halting of the flow of the liquid by said first valve arrangement to permit flow of said carrier gas to said head space chamber to carry the gaseous phase of the water to said detector prior to the water molecules in the liquid sample and the water molecules escaped from the liquid sample reaching equilibrium.

11. The analyzer of claim 10 wherein said detector is an electrolytic moisture detecting cell.

12. The analyzer of claim 10 wherein said liquid sample is taken from its source at a point where the pressure of said liquid is greater than atmospheric.

13. The analyzer of claim 12 further including a return flow path for the liquid sample from the head space chamber back to its source at a point that has a pressure greater than atmospheric, said first valve arrangement providing for flow through said return flow path when actuated to permit flow to said head space chamber and halting flow back to said source when flow to said chamber is halted.

14. The analyzer of claim 13 wherein the pressure of said source at the point at which the liquid sample is returned has a pressure less than the pressure of the source at the point at which the liquid is taken from the source.

15. The analyzer of claim 10 wherein said controller causes the actuation of said second valve arrangement to halt the flow of carrier gas to said head space chamber and thereafter causes the action of the first valve arrangement to causes the liquid sample to again flow to said chamber to replenish the liquid therein.

16. The analyzer of claim 10 wherein said controller performs a sequence of:
    passing the water molecules in the liquid sample through said head space chamber;
    controlling the flow of the liquid sample from its source to said head space chamber at a constant temperature;

detecting the presence of water in said liquid sample;

providing a source of water-free carrier gas;

controlling the flow of said water-free carrier gas from its source to said head chamber; and providing a fixed volume of said liquid sample from its source to said head space chamber and thereafter halting the flow thereto, and activating the second valve arrangement after the halting of the flow of the liquid by the first valve arrangement to permit flow of said carrier gas to said head space chamber to carry the gaseous phase of the water to said detector prior to the water molecules in the liquid sample and the water molecules escaped from the liquid sample reaching equilibrium; thereby providing repetitive monitoring.

17. The analyzer of claim 10 wherein said head space chamber has a liquid inlet port and a liquid outlet port, and further comprising a liquid inlet line connected to said liquid inlet port and a liquid outlet line connected to said liquid outlet port, said first valve arrangement including a first valve in said liquid inlet line and a second valve in said liquid outlet line.

18. The analyzer of claim 17 wherein said second valve arrangement includes a fluid control valve moveable between an deactivated position and an activated position, said valve in said deactivated position directing flow of said water-free carrier gas from its source directly to the detector and in its active position directing said flow of carrier gas to said head space chamber and then to said detector.

19. The analyzer of claim 18 wherein said fluid control valve is actuated by operating air, and further including a solenoid valve for controlling flow of operating air to said fluid control valve, said solenoid valve being moveable between a de-energized position and an energized position, said solenoid valve in said de-energized position providing operating air to said fluid control valve to hold said fluid control valve in its deactivated position, and in its energized position providing operating air to said fluid control valve to hold said fluid control valve in its activated position.

20. The analyzer of claim 17 wherein said first valve in said liquid inlet line and said second valve in said liquid outlet line are actuated by operating air, and further including a solenoid valve for controlling flow of operating air to said first and second valves, said solenoid valve being moveable between a de-energized position and an energized position, said solenoid valve in said de-energized position venting air from first and second valves to cause the first and second valves to be in a deactivated position in which the flow of liquid sample to and from the head space chamber is blocked, and in said energized position causing control air to flow to the first and second valves to move said first and second valves into an active position permitting flow of liquid sample to and from said head space chamber.

* * * * *